United States Patent
Polkus et al.

(10) Patent No.: US 6,422,749 B1
(45) Date of Patent: Jul. 23, 2002

(54) IMAGING SYSTEM WITH X-RAY BEAM ANGULATION COMPENSATION

(75) Inventors: Vincent S. Polkus, Delafield; Alexander Ganin, Whitefish Bay; Jon C. Omernick, Wauwatosa; Ping Xue, Cottage Grove, all of WI (US)

(73) Assignee: General Electric Company, Waukesha, WI (US)

( * ) Notice: Subject to any disclaimer, the term of this patent is extended or adjusted under 35 U.S.C. 154(b) by 222 days.

(21) Appl. No.: 09/615,475

(22) Filed: Jul. 13, 2000

(51) Int. Cl.$^7$ .................................................. A61B 6/08
(52) U.S. Cl. ............................. 378/205; 378/11; 378/19
(58) Field of Search ................................. 378/4, 11, 19, 378/145, 205, 12, 14, 16, 138, 163

(56) References Cited

U.S. PATENT DOCUMENTS

| | | | |
|---|---|---|---|
| 4,008,400 A | * 2/1977 | Brunnett et al. | 378/4 |
| 4,024,403 A | 5/1977 | Bernstein et al. | 250/445 R |
| 6,056,437 A | * 5/2000 | Toth | 378/205 |
| 6,148,058 A | * 11/2000 | Dobbs | 378/19 |

FOREIGN PATENT DOCUMENTS

DE 90 02 129 4/1990

OTHER PUBLICATIONS

European Search Report, EP 01 30 6074, dated Oct. 26, 2001.

* cited by examiner

Primary Examiner—Robert H. Kim
Assistant Examiner—Therese Barber
(74) Attorney, Agent, or Firm—Jenkens & Gilchrist

(57) ABSTRACT

In an X-ray imaging system, an arrangement is provided for readily aligning the system detector with the X-ray beam field, i.e., the projection of the X-ray beam into the plane of the detector. The arrangement is adapted for correcting or compensating for distortion which results from X-ray beam angulation, wherein the beam is projected toward the detector plane at an angle of less than 90°. Initially, the system X-ray tube is positioned to project the X-ray beam at a given beam direction angle $\phi$. A beam width angle $\gamma_1$ is then computed, from the given angle $\phi$ and from specified values of the source-to-image distance and the length of the projected beam field. Thereupon, an offset value is determined from $\gamma_1$, $\phi$ and the source-to-image distance to locate the geometric center of the beam field, and the center of the detector is aligned therewith.

20 Claims, 3 Drawing Sheets

IMAGING SYSTEM WITH X-RAY BEAM ANGULATION COMPENSATION

BACKGROUND OF THE INVENTION

The invention disclosed and claimed herein generally pertains to a method and apparatus for correcting or compensating for distortion of the shape of the X-ray field in an X-ray imaging system. More particularly, the invention pertains to a method of the above type wherein distortion results from X-ray beam angulation, that is, projection of the X-ray beam toward the X-ray detector at an angle of less than 90 degrees. Even more particularly, the invention pertains to a method of the above type wherein the geometric center of the X-ray beam field, as projected into the plane of the detector and distorted by the angulation, is computed and selectively positioned with respect to the detector.

As is well known, in a typical X-ray imaging system a patient is positioned between an X-ray tube and an image receptor having a planar imaging surface, such as an X-ray film or a digital solid state detector. The tube projects a beam of X-radiation toward the detector surface and through body structure of the patient which is to be imaged. The area of projected X-radiation which is incident on the detector defines the active imaging area (AIA). Generally, the X-ray beam field or field of view (FOV), which is defined herein to be the intersection of the projected beam and the detector plane, must be coincident with, or lie within, the boundaries of the detector surface in order to avoid loss of image data. The FOV may be adjusted by rotating or tilting the tube to vary the direction of the projected X-ray beam, and also by operating a collimator to vary the width and length dimensions of the X-ray beam. Further adjustments may be made by linear translation of the tube and/or the detector If the tube is oriented so that the X-ray beam, or more particularly the beam axis or central ray thereof, is directed in perpendicular or orthogonal relationship to the detector plane, the beam field projected into the detector plane will be of rectangular configuration. However, an X-ray technician or operator, when setting up for an imaging procedure, may need to angulate the beam, that is, rotate or pivot the X-ray tube so that the beam is directed toward the detector at an angle of less than 90 degrees. This may be necessary, for example, to ensure that the beam passes through the specific body structure of the patient which is to be imaged. As the X-ray beam is increasingly angulated, however, the beam field projected into the detector becomes correspondingly distorted and trapezoidal, and the location of the center of the central ray of the beam becomes offset with respect to the geometric center of the projected X-ray field. As a consequence of these decentering and distorting effects, the task of the operator to achieve alignment becomes more difficult, time consuming and prone to error. More specifically, it may become necessary for the operator to re-collimate the X-ray beam to a smaller field size, or to realign the image detector with the beam field, in order to achieve optimal centering of the projected image onto the detector. It may also be necessary to reposition the patient. In the absence of optimal or appropriate centering, anatomical cutoff may occur during the imaging process, which would necessitate that the examination be repeated, thus contributing to increased procedure cycle time, higher examination costs, and higher net radiation doses to the patient. Moreover, if beam angulation causes the angle of beam incidence to exceed +/−10°, current regulations prevent use of an automated device to adjust the collimator. Accordingly, the system operator must manually collimate the beam to a desired field size.

SUMMARY OF THE INVENTION

The invention relates to an arrangement for enabling an operator of an X-ray system to quickly and efficiently align the X-ray detector with the imaging subject and the projected X-ray beam, in a manner which avoids anatomical cutoff and inaccurate positioning, notwithstanding any angulation of the beam or distortion effects resulting therefrom. Moreover, the invention reduces cycle time by enabling autocollimation for angles of beam incidence in excess of +/−10°, and by providing for automatic shifting of the detector.

One embodiment of the invention is directed to a method of alignment for an imaging system provided with an X-ray tube and a detector having a surface lying in a specified plane, wherein the tube is spaced apart from the detector by a source-to-image distance (SID) along a first axis, and wherein the tube is disposed to project an X-ray beam characterized by a beam direction angle $\phi$ and a beam width angle $\gamma$ toward the detector. The method includes the step of specifying the length dimension of the beam field projected into the specified detector plane, the length dimension being measured along a second axis which is orthogonal to the first axis. The method further comprises the steps of computing a value of the beam width angle from the specified beam field length, the SID and the beam direction angle, and then locating the geometric center of the beam field from the computed beam width angle, the SID and the beam direction angle. Thereupon, a selected positional relationship is established between the center of the detector surface and the geometric center of the beam field.

In a preferred embodiment of the invention, the locating step comprises determining the point at which the central axis of the projected beam intersects the detector plane, and then locating the geometric center at a point which is spaced apart from the beam axis intersection point, along the second axis, by a computed offset value. The offset value is computed from the SID and beam direction angle, and also from the computed value of the beam width angle. Preferably also, the center of the detector surface is aligned with the geometric center of the beam field, after the offset value has been determined. In one useful embodiment, the specified length of the beam field is equal to the length of the detector surface extending along the second axis. In another useful embodiment, the specified length of the beam field is selectively less than the length of the detector surface along the second axis.

DETAILED DESCRIPTION OF THE PREFERRED EMBODIMENT

Figure 1:
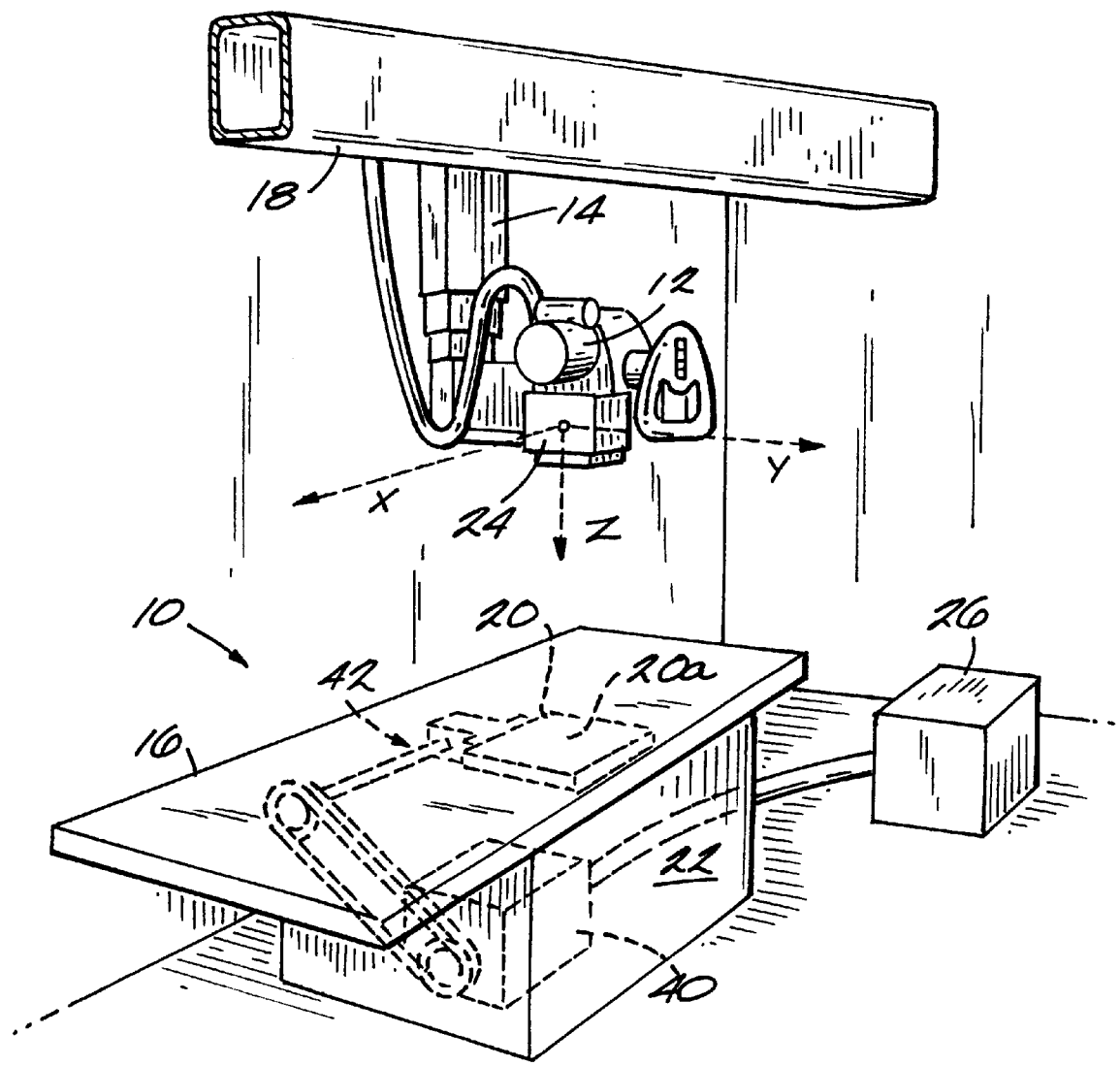
FIG. 1 is a perspective view showing components of an X-ray imaging system for use in connection with an embodiment of the invention.

Referring to FIG. 1, there is shown an X-ray imaging system 10 provided with an X-ray tube 12 which is journalled or pivotably mounted on a vertically oriented column 14. System 10 further includes a table 16 which is disposed to support a patient or other imaging subject (not shown in FIG. 1) in a horizontal plane. Usefully, column 14 is suspended from a track 18, and the tube and column may be translated along the track and along the length dimension of table 16. FIG. 1 further shows table 16 carried upon a table base 22, which also supports a flat X-ray detector 20 directly beneath the table 18. Detector 20 has a planar image receiving surface 20a, and usefully comprises X-ray film or a digital solid state detector.

It is to be understood that horizontal support of a patient is shown in FIG. 1 for purposes of illustration, and is by no means intended to limit the scope of the invention. In other embodiments the patient could be placed in a vertical or other orientation, provided that the X-ray tube and detector were respectively located so that the patient was positioned between them.

After an imaging subject has been placed on table 16, X-ray tube 12 is adjusted to project a beam of X-radiation through a region of the subject to image specified body structure. The tube position may be adjusted by pivoting the tube relative to column 14, and also by translating the column and tube along the table. The dimensions of the projected X-ray beam may be adjusted by means of a collimator 24, of conventional design, which is joined to tube 12 and is traversed by the projected beam. Detector 20 is likewise mounted for translational movement along the table 16, and is disposed to receive the image of the specified body structure. However, as stated above, the detector must be properly aligned with the projected beam field or FOV, in order to ensure detection of all desired image data. Usefully, means may be provided for automatically aligning the detector and the beam field. Referring further to FIG. 1, there is shown an electronic device 26 for performing computations in accordance with an embodiment of the invention, as described hereinafter, and for controlling operation of the alignment means. FIG. 1 also shows mutually orthogonal X-, Y-, and Z- coordinate axes for reference purposes, the Z-axis being vertically oriented, the X-axis being parallel to the longitudinal dimension of table 16, and the Y-axis being transverse thereto. The center of the coordinate system is coincident with the focal spot of X-ray tube 12, and the tube is mounted for rotation about the center of the coordinate system.

Figure 2:
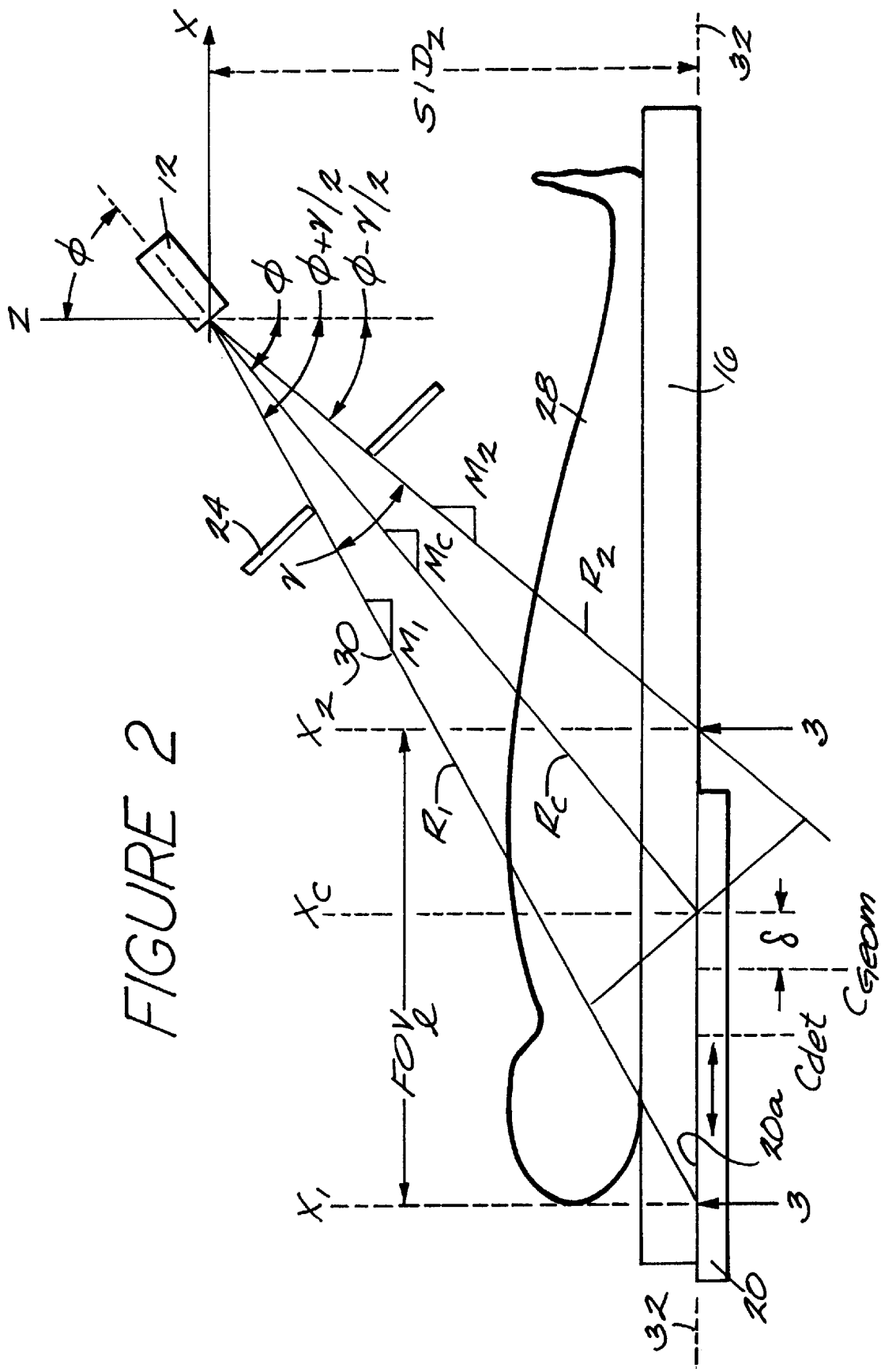
FIG. 2 is a schematic diagram showing components of the system of FIG. 1 in simplified form, together with an imaging subject, to illustrate principles of an embodiment of the invention.

Referring to FIG. 2, there is shown tube 12 oriented to project an X-ray beam 30 toward detector 20, through a patient 28 positioned on table 16. More specifically, tube 12 is directed so that its central ray $R_c$, comprising the beam axis, is at an angle $\phi$ with respect to the vertical Z-axis, wherein $\phi$ may be 45° and is hereinafter referred to as the beam direction angle. However, it is to be understood that the principles of the invention apply to any beam direction angle $\phi$ which is less than +/−90°. It is to be further understood that central ray $R_c$ of beam 30 is directed toward detector surface 20a at an angle of 90° if $\phi$ is 0°, and is directed toward the detector surface at an angle of less than 90° if $\phi$ is non-zero. Thus, beam 30 is angulated, as described above, when $\phi$ is non-zero. FIG. 2 further shows projected beam 30 to be bounded in the X-Z plane by rays $R_1$ and $R_2$ extending along its respective edges. FIG. 2 also shows beam 30 passing through collimator 24. Collimator 24 establishes the angle $\gamma$ of beam 30 in the X-Z plane, the collimator 24 being adjustable to selectably vary $\gamma$. Hereinafter, $\gamma$ is referred to as the beam width angle. Since central ray $R_c$ of beam 30 is at an angle $\phi$, it will be readily apparent that rays $R_1$ and $R_2$ are oriented to angles of $\phi+\gamma/2$ and $\phi-\gamma/2$, respectively, as shown by FIG. 2.

Referring further to FIG. 2, there is shown X-ray beam 30 intersecting detector plane 32, the plane of detector surface 20a of detector 20. This intersection defines the beam field or FOV, that is, the projection of the beam into the detector plane. The length $FOV_1$ of the beam field, i.e., its dimension along the X-axis, is the distance between $X_1$ and $X_2$, the points at which detector plane 32 is intersected by rays $R_1$ and $R_2$, respectively, of X-ray beam 30. In order to align the beam FOV with detector surface 20a, it is necessary to know the location of the beam FOV along the X-axis, with respect to a known reference point.

Figure 3:
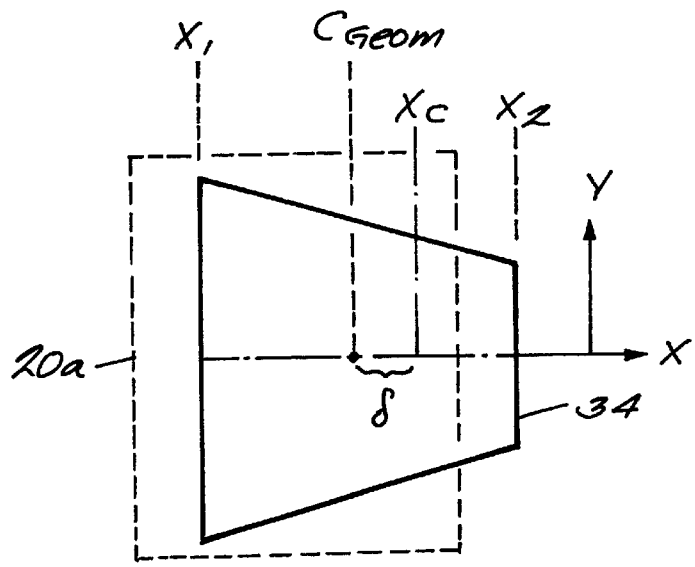
FIG. 3 is a view taken along lines 3—3 of FIG. 2, illustrating distortion of the beam field which results from X-ray beam angulation.

Referring further to FIG. 2, it is seen that $X_c$, the point at which beam axis $R_c$ intersects the detector plane, and which may serve as a useful reference in aligning the detector and beam field, may be readily determined from $\phi$ and $SID_z$. More particularly, $X_c$ equals $SID_z \tan\phi$, where $SID_z$ is the source-to-image distance along the Z-axis, i.e., the distance between the tube 12 and the detector plane 32, which is a known value. Moreover, as stated above, when X-ray beam 30 is angulated, by pivoting tube 12 to a non-zero angle of $\phi$, the beam field projected into the detector plane 32 becomes distorted, and the geometric center thereof is shifted away from $X_c$. This is illustrated by FIG. 3, wherein the beam field 34 of beam 30, which is projected into detector plane 32 as described above, is shown to be of trapezoidal configuration. Also, FIG. 3 shows beam axis intersection $X_c$ to be offset from the geometric center $C_{geom}$ of beam field 34 by an amount $\delta$. As a result, as illustrated by both FIGS. 2 and 3, a portion of beam field 34 is not incident upon detector 20, whereby the image data provided by such beam portion is not received. In order to properly align beam field 34 and detector surface 20a, so that data is not lost, it becomes necessary to determine the offset value $\delta$.

While FIG. 2 shows beam 30 angulated by pivoting tube 12 with respect to the Z-axis, the beam could alternatively be angulated by pivoting or rotating detector 20. Generally, the invention is applicable for any relative movement between the tube and the detector which causes the beam direction angle $\phi$ to become less than +/−90°.

Figure 4:
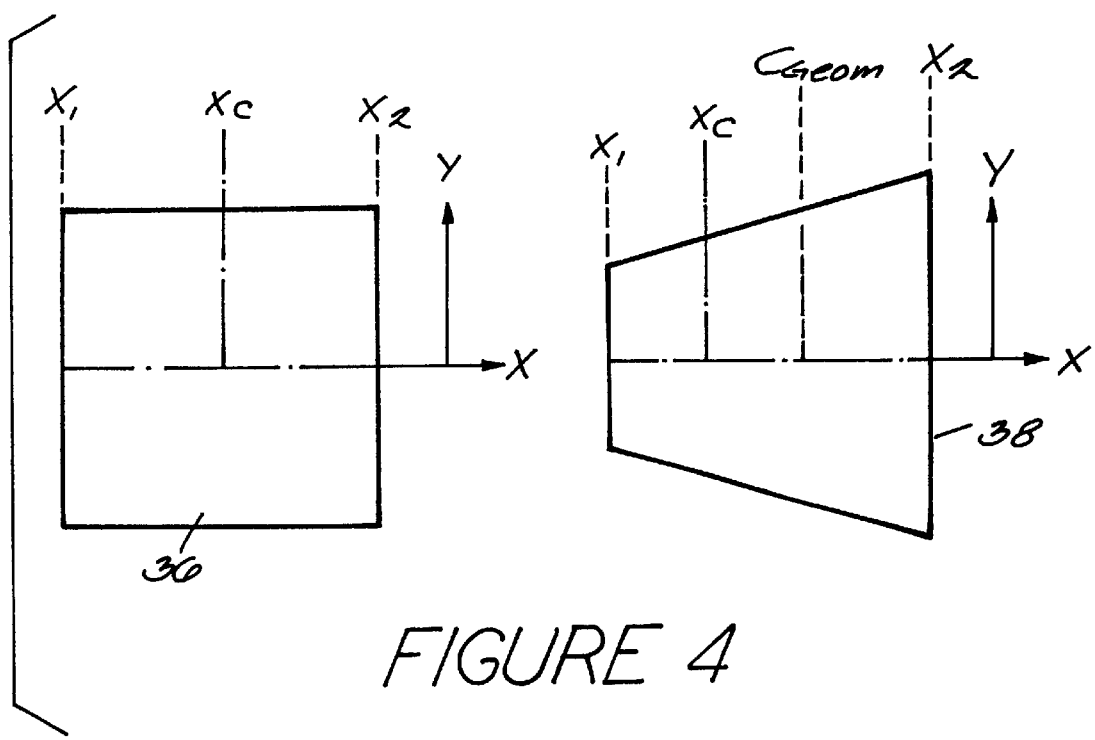
FIG. 4 shows two other beam fields for comparison with the field of FIG. 3.

Referring to FIG. 4, there is shown, by way of comparison, the beam field 36 which results when $\phi$ is set to 0°, so that tube 12 projects an X-ray beam toward the detector plane at an angle of 90°. The beam field 36 is of symmetrical rectangular shape, and the geometric center coincides with the point $X_c$.

Referring further to FIG. 4, there is shown the beam field 38 which results when $\phi$ is set to a value such as −45°. The beam field 38 is seen to be trapezoidal, in like manner with beam field 34 of FIG. 3, but is distorted in the opposite direction. Also, in beam field 38 the point $X_c$ is offset leftward from the geometric center, along the X-axis, rather than rightward as shown in connection with beam field 34.

In determining the value of offset $\delta$, it is useful to first consider the slopes $M_1$, $M_2$ and $M_c$, the slopes of rays $R_1$, $R_2$ and $R_c$, respectively, as shown by FIG. 2. Each of these slopes can be defined in terms of the defined angles $\phi$ and $\delta$, as follows:

$$M_{center} = \tan(\phi) \quad\quad \text{Equation (1)}$$

$$M_1 = \tan(\phi+\gamma/2) \quad\quad \text{Equation (2)}$$

$$M_2 = \tan(\phi-\gamma/2) \quad\quad \text{Equation (3)}$$

For the coordinate system described above for the X-Z plane shown in FIG. 2, the equation for a line shown therein has the generalized form $x_i = M_i z_i + b_i$, where $(x_i, z_i)$ are coordinates of points along the line and $M_i$ is its slope. However, computational complexity can be reduced if imaging system 10 is designed so that the focal spot of tube 12 is coincident with the rotation center of the X-ray tube support device. In this case, the equations pass through the origin of the coordinate system, and the $b_i$ terms drop to 0, resulting in the expression $x_i = M_i z_i$, which is useful for describing beam rays $R_1$, $R_2$ and $R_c$. Moreover, for $z_i = SID_z$, the known source-to-image distance, respective intersection points $X_1$ and $X_2$ of rays $R_1$ and $R_2$ are given as follows:

$$X_1 = M_1 SID_z = SID_z \tan(\phi + \gamma/2) \quad \text{Equation (4)}$$

$$X_2 = M_2 SID_z = SID_z \tan(\phi - \gamma/2) \quad \text{Equation (5)}$$

It is essential to recognize that the length $FOV_1$ of beam field 34 can be no less than the length dimension of detector surface 20a which extends along the X-axis. Thus, $FOV_1$ of beam field 34 is prespecified to either be equal to, or selectively less than, the length of detector surface 20a. Thus, $FOV_1$ is a known predetermined value. From FIG. 2, it is seen that $FOV_1$ is equal to $(X_1 - X_2)$. Accordingly, $FOV_1$ is related to $SID_z$, $\phi$ and $\gamma$ as follows:

$$FOV_1 = X_1 - X_2 = SID_z[\tan(\phi + \gamma/2) - \tan(\phi - \gamma/2)] \quad \text{Equation (6)}$$

Using the known trigonometric relationships $$\tan(A - B) = \frac{\tan A - \tan B}{1 + \tan A \tan B}$$

and $$\tan(A + B) = \frac{\tan A + \tan B}{1 - \tan A \tan B},$$

Equation (6) can be rearranged as follows:

$$FOV_1 = \left[ \frac{2(1 + \tan^2(\phi)) \tan\left(\frac{\gamma}{2}\right)}{1 - \tan^2(\phi) \tan^2\left(\frac{\gamma}{2}\right)} \right] \times SID_z \quad \text{Equation (7)}$$

When the terms of Equation (7) are re-arranged and the equation solved, the following quadratic results:

$$A \tan^2(\gamma/2) + B \tan(\gamma/2) + C = 0 \quad \text{Equation (8)}$$

where $A = \tan^2(\phi)$, $B = 2(1 + \tan^2(\phi)) \times (SID_z/FOV_1)$, and $C = -1$. Solution of the quadratic Equation (8) gives rise to two possible solutions $$\gamma_1 = \quad \text{Equation (9)}$$

$$2\tan^{-1}\left[ \frac{-\left(\frac{1 + \tan^2(\phi)}{FOV_1/SID_z}\right) + \sqrt{\left(\frac{1 + \tan^2(\phi)}{FOV_1/SID_z}\right)^2 + \tan^2(\phi)}}{\tan^2(\phi)} \right]$$

$$\gamma_2 = 2\tan^{-1}\left[ \frac{-\left(\frac{1 + \tan^2(\phi)}{FOV_1/SID_z}\right) - \sqrt{\left(\frac{1 + \tan^2(\phi)}{FOV_1/SID_z}\right)^2 + \tan^2(\phi)}}{\tan^2(\phi)} \right]$$

Equation (10)

For the geometric state of the X-ray beam provided by imaging system 10, only the solution $\gamma_1$ provided by Equation (9) is valid. Thus, after $\gamma_1$ has been determined, collimator 24 is adjusted as required to establish the beam width angle of beam 30 at $\gamma_1$. The length $FOV_1$ is thereby set to the value prespecified therefor. Moreover, from the values of $FOV_1$, beam direction angle $\phi$, $SID_z$ and $\gamma_1$, the offset $\delta$ can be directly computed, in order to establish the required displacement of the detector for alignment to the center of the projected X-ray field. To compute $\delta$, it is noted that the geometric center $C_{geom}$ of the projected beam field 34 is defined by the average $\overline{X}$ of the coordinates $X_1$ and $X_2$, that is, $\overline{X} = (X_{+(X1)} + X_2)/2$. From Equations (4) and (5) for $\gamma = \gamma_1$, $\overline{X}$ may be set forth as follows:

$$\overline{X} = \frac{SID_z}{2}\left(\tan\left(\phi + \frac{\gamma_1}{2}\right) + \tan\left(\phi - \frac{\gamma_1}{2}\right)\right) \quad \text{Equation (11)}$$

As stated above, $X_c$ is equal to $SID_z \tan(\phi)$. Thus, the offset $\delta$ given by the expression:

$$\delta = \overline{X} - X_c = SID_z \left[ \frac{\left(\tan\left(\phi + \frac{\gamma_1}{2}\right) + \tan\left(\phi - \frac{\gamma_1}{2}\right)\right)}{2} - \tan(\phi) \right] \quad \text{Equation (12)}$$

Electronic control device 26, shown in FIG. 1 and comprising a computer control or the like, is disposed to receive the specified values of $\phi$, $SID_z$ and $FOV_1$ as inputs, and is configured to perform computations in accordance with the equations set forth above. Thus, upon receiving the specified inputs, device 26 is operated to implement Equations (7)–(9) to determine the beam width angle $\gamma_1$ corresponding to the inputs. If collimator 24 is automatically adjustable, in response to a signal, control device 26 may be further configured to couple a signal, representing $\gamma_1$ to adjust collimator 24, and thereby provide autocollimation.

After determining $\gamma_1$, control device 26 is operated in accordance with Equations (11) and (12) to compute offset $\delta$. If imaging system 10 is provided with a servo mechanism 40, as shown by FIG. 1, control device 26 may couple a signal representing offset $\delta$ to direct servo mechanism 40 to align the center of detector 20 with point $C_{geom}$, as described above. FIG. 1 further shows a mechanical linkage 42, such as a rotatable ball screw and ball nut arrangement, for enabling mechanism 40 to selectively translate detector 20 along the X-axis. Thus, an embodiment of the invention may be provided in which both detector alignment and collimation are performed automatically.

In another embodiment of the invention, control device 26 would provide information to the system operator, for use in manual adjustment of the detector and/or the collimator.

The above description in regard to electronic control device 26 is directed to a mode of the invention wherein specified values of $FOV_1$, $\phi$, and $SID_z$ are given. Accordingly, the required computational task is determination of the beam width angle $\gamma_1$, and then determination of the offset value $\delta$, using the equations respectively given therefor. In a second mode of the invention, $\gamma_1$ is initially given, together with the values of $\phi$ and $SID_z$. In this mode it would only be necessary to compute the offset $\delta$, using Equations 11 and 12. This situation could occur, for example, if $FOV_1$ was preselected and the value of $\gamma_1$ associated therewith was initially known for the given image parameters.

Obviously, many other modifications and variations of the present invention are possible in light of the above teachings. It is therefore to be understood that within the scope of the disclosed concept, the invention may be practiced otherwise than as has been specifically described.

What is claimed is:

1. In an imaging system provided with an X-ray tube and a detector having a surface lying in a specified plane, wherein said tube is spaced apart from said detector surface by a source-to-image distance along a first axis, and wherein said tube is disposed to project an X-ray beam characterized by beam direction and beam width angles toward said detector, a method for selectively aligning said detector surface and the field of said beam which is projected into said specified plane, said method comprising the steps of:

providing a value of said beam width angle;

locating the geometric center of said beam field from said distance, said beam direction angle and said beam width angle value; and establishing a specified positional relationship between the center of said detector surface and said geometric center of said beam field along a second axis which is orthogonal to said first axis.

2. The method of claim 1 wherein said locating step comprises:

determining the point at which the central axis of said projected beam intersects said specified plane; and locating said geometric center at a point which is spaced apart from said beam axis intersection point, along said second axis, by an offset value comprising a function of said distance, said beam direction angle and said computed beam width angle.

3. The method of claim 2 wherein:

said beam width angle value is provided by specifying the dimension of said beam field along said second axis, and then computing said beam width angle value from said specified beam field dimension, said distance and said beam direction angle.

4. The method of claim 3 wherein:

said positional relationship is established by aligning the center of said detector surface and said geometric center of said beam field along a common axis.

5. The method of claim 4 wherein:

said specified dimension of said beam field is equal to the length of said detector surface extending along said second axis.

6. The method of claim 3, wherein said imaging system is provided with an electronic control device disposd to receive input signals respectively representing said specified beam field dimension, said distance, and said beam direction angle, and wherein:

said method includes the step of operating said control device to automatically compute said corresponding beam width angle and said offset value from said received input signals.

7. The method of claim 6 wherein:

said method includes the step of coupling an output signal from said control device to an associated mechanical device to operate said mechanical device to align said detector surface center with said beam field geometric center.

8. The method of claim 7 wherein:

said control device operates a collimator associated with said projected beam to adjust said beam width angle to said computed value thereof.

9. In an imaging system provided with an X-ray tube and a detector having a surface lying in a specified plane, wherein said tube is spaced apart from said detector surface by a source-to-image distance (SID) along a first axis, a method for positioning said tube and said detector with respect to a patient supported therebetween, said method comprising the steps of:

orienting said tube to project an X-ray beam through a selected region of said patient and toward said specified plane, the central axis of said projected beam being placed at an angle $\phi$ with respect to said first axis;

specifying the length, along a second axis orthogonal to said first axis, of a beam field defined by the intersection of said beam and said specified plane;

computing a beam width angle $\gamma_1$ which provides said specified beam field length for said angle $\phi$ and for said SID;

employing the respective values of $\gamma_1$, $\phi$, and SID to determine the location of the geometric center of said beam field; and establishing a specified positional relationship between the center of said detector surface and said geometric center of said beam field.

10. The method of claim 9 wherein:

the location of said geometric center is determined by computing an offset value as a function of $\gamma_1$, $\phi$, and SID, and by locating the point at which said central beam axis intersects said specified plane, said geometric center being spaced apart from said beam axis intersection point, along said second axis, by said offset value.

11. The method of claim 10 wherein:

said positional relationship is established by aligning the center of said detector surface and said geometric center of said beam field along a common axis.

12. The method of claim 11 wherein:

said specified length of said beam field is equal to the length of said detector surface extending along said second axis.

13. The method of claim 11 wherein:

said specified length of said beam field is selectively less than the length of said detector surface extending along said second axis.

14. An X-ray imaging system comprising:

a detector having a surface lying in a specified plane;

an X-ray tube spaced apart from said detector surface by a source-to-image distance (SID) along a first axis, said tube being rotatable to an angle $\phi$, with respect to said first axis, to project an X-ray beam through a selected region of an imaging subject and toward said specified plane;

a collimator traversed by said projected beam which is disposed to selectively adjust the width angle thereof, and to thereby adjust the length, along a second axis orthogonal to said first axis, of a beam field defined by the intersection of said beam and said specified plane;

an electronic control device disposd to receive input signals respectively representing a specified value of said beam field length, said SID, and said angle $\phi$, and to generate an output signal therefrom representing the location of the geometric center of said beam field; and an alignment device responsive to said output signal to establish a specified positional relationship between the center of said detector surface and said geometric center of said beam field.

15. The system of claim 14 wherein:

said control device is adapted to compute a beam width angle $\gamma_1$ which provides said specified beam field length for said SID and said angle $\phi$.

16. The system of claim 15 wherein:

said control device is adapted to determine the location of said geometric center by computing an offset value as a function of $\gamma_1$, $\phi$, and SID, and by locating the point at which the central axis of said beam intersects said specified plane, said geometric center being spaced apart from said beam axis intersection point, along said second axis, by said offset value.

17. The system of claim 16 wherein:

said positional relationship is established by aligning the center of said detector surface and said geometric center of said beam field along a common axis.

18. The system of claim 17 wherein:

said specified length of said beam field is equal to the length of said detector surface extending along said second axis.

19. The system of claim 17 wherein:

said specified length of said beam field is selectively less than the length of said detector surface extending along said second axis.

20. The system of claim 17 wherein:

said control device couples a second output signal representing said angle $\gamma_1$ to said collimator, said collimator being operable in response to said second output signal to adjust said beam to provide said specified beam field length.

* * * * *